United States Patent
Ely (10) Patent No.: US 9,445,177 B2
(45) Date of Patent: Sep. 13, 2016

(54) HEARING DEVICE TETHER WITH ACOUSTIC DECOUPLING SECTION

(71) Applicant: 3M INNOVATIVE PROPERTIES COMPANY, St. Paul, MN (US)

(72) Inventor: Jacob H. Ely, Indianapolis, IN (US)

(73) Assignee: 3M Innovative Properties Company, St. Paul, MN (US)

( * ) Notice: Subject to any disclaimer, the term of this patent is extended or adjusted under 35 U.S.C. 154(b) by 137 days.

(21) Appl. No.: 14/082,790

(22) Filed: Nov. 18, 2013

(65) Prior Publication Data

US 2015/0139470 A1     May 21, 2015

(51) Int. Cl.
| | | |
|---|---|---|
| A61F 11/06 | (2006.01) | |
| H04R 1/10 | (2006.01) | |
| A61F 11/08 | (2006.01) | |
| A61F 11/12 | (2006.01) | |

(52) U.S. Cl.
CPC ............. *H04R 1/1033* (2013.01); *A61F 11/08* (2013.01); *A61F 11/12* (2013.01); *H04R 1/1066* (2013.01)

(58) Field of Classification Search
CPC . H04R 1/1016; H04R 1/1083; H04R 1/1033
USPC ................. 381/320, 328, 370, 372, 382
See application file for complete search history.

(56) References Cited

U.S. PATENT DOCUMENTS

| | | |
|---|---|---|
| 4,193,396 A | 3/1980 | Wacker |
| 4,219,018 A | 8/1980 | Draper, Jr. |
| 4,314,553 A | 2/1982 | Westerdal |
| D277,317 S | 1/1985 | Eisenmenger |
| 4,806,186 A | 2/1989 | Sirkin |
| 4,867,149 A | 9/1989 | Falco |
| 4,936,411 A | 6/1990 | Leonard |
| 5,475,449 A | 12/1995 | Pyle |
| 5,541,677 A | 7/1996 | Huhtala |
| 5,581,821 A | 12/1996 | Nakano |
| 5,668,354 A | 9/1997 | Falco |
| 5,711,313 A | 1/1998 | Fleming |
| 5,727,566 A | 3/1998 | Leight |
| 5,749,373 A | 5/1998 | Dix |
| 5,799,658 A | 9/1998 | Falco |
| 5,806,526 A | 9/1998 | Rhoad |
| 6,074,060 A | 6/2000 | Bruce |
| 6,148,821 A | 11/2000 | Falco |
| 6,340,227 B1 | 1/2002 | Solberg |

(Continued)

FOREIGN PATENT DOCUMENTS

| | | |
|---|---|---|
| CN | 100544688 | 9/2009 |
| CN | 201435806 | 3/2010 |

(Continued)

OTHER PUBLICATIONS

International Application PCT/US2014/064267 Search Report dated Jan. 21, 2015.

*Primary Examiner* — Paul S Kim
*Assistant Examiner* — Norman Yu
(74) *Attorney, Agent, or Firm* — Kenneth B. Wood (57) ABSTRACT

A hearing article having an acoustic decoupling section is provided. In an exemplary embodiment, a hearing article described herein includes a tether having a first end attached to a first hearing device, a first acoustic decoupling section proximate the first end, and a substantially straight intermediate section. The acoustic decoupling section comprises a predetermined shape.

21 Claims, 4 Drawing Sheets

(56) References Cited

U.S. PATENT DOCUMENTS

| | | |
|---|---|---|
| 6,440,339 B1 | 8/2002 | Magidson |
| 6,568,394 B2 | 5/2003 | Falco |
| 6,801,629 B2 | 10/2004 | Brimhall |
| 6,938,622 B2 | 9/2005 | Huang |
| 7,185,734 B2 | 3/2007 | Widmer |
| 7,210,484 B1 | 5/2007 | Tiemens |
| 7,213,916 B1 | 5/2007 | Pettett |
| 7,370,655 B2 | 5/2008 | Taylor |
| 7,457,428 B2 * | 11/2008 | Vaudrey et al. ............... 381/372 |
| 7,464,786 B2 | 12/2008 | Falco |
| 7,551,940 B2 | 6/2009 | Paulson |
| 7,594,724 B2 | 9/2009 | Purcell |
| 7,712,469 B2 | 5/2010 | Jenkins, Jr. |
| 8,333,260 B1 | 12/2012 | Hall |
| 8,655,006 B2 * | 2/2014 | Aase ..................... B29C 43/203 381/370 |
| 2004/0045558 A1 | 3/2004 | Taylor |
| 2004/0079579 A1 | 4/2004 | Barwacz |
| 2005/0274568 A1 | 12/2005 | Falco |
| 2006/0042867 A1 | 3/2006 | Haussmann |
| 2007/0036376 A1 * | 2/2007 | Fried ............................. 381/312 |
| 2009/0041261 A1 | 2/2009 | Fickweiler |
| 2009/0199326 A1 | 8/2009 | Brauner |
| 2009/0314515 A1 | 12/2009 | Bevirt |
| 2011/0051974 A1 * | 3/2011 | Liu ........................ B82Y 30/00 381/370 |
| 2011/0131709 A1 | 6/2011 | Caraballo |
| 2012/0150249 A1 * | 6/2012 | Faller et al. ..................... 607/5 |
| 2013/0022228 A1 | 1/2013 | Kuhtz |
| 2013/0163803 A1 | 6/2013 | Erdel |

FOREIGN PATENT DOCUMENTS

| | | |
|---|---|---|
| CN | 201805528 | 4/2011 |
| CN | 202135285 | 2/2012 |
| CN | 202713574 | 3/2013 |
| EP | 0244979 | 4/1987 |
| EP | 2311406 | 4/2011 |
| JP | 3019038 | 5/1995 |
| JP | 2004-187745 | 7/2004 |
| KR | 2010-0008120 | 8/2010 |
| WO | WO 2008/014172 | 1/2008 |

* cited by examiner

HEARING DEVICE TETHER WITH ACOUSTIC DECOUPLING SECTION

TECHNICAL FIELD

This disclosure relates to a hearing article, in particular a hearing article including a tether having a first end attached to a hearing device and an acoustic decoupling section proximate the first end.

BACKGROUND

The use of hearing protective and noise attenuating devices are well known, and various types of devices have been considered. Such devices include earplugs and semi-aural devices that may be inserted into, or placed over, the ear canal of a user to obstruct passage of sound waves to the inner ear. Various techniques have been considered for maintaining hearing protective devices, such as maintaining two hearing devices together as a pair, including use of a tether or cord joined to two hearing devices.

SUMMARY

The present disclosure provides a hearing article including first and second hearing devices and a tether having a first end attached to the first hearing device and a second end attached to a second hearing device. The tether includes a first acoustic decoupling section proximate the first end, a second acoustic decoupling section proximate the second end, and a substantially straight intermediate section between the first and second acoustic decoupling sections. The first and second acoustic decoupling sections include first and second predetermined shapes.

The present disclosure further provides a hearing article including a first hearing device, an attachment device and a tether having a first end attached to the first hearing device and a second end attached to the attachment device. The tether includes a first acoustic decoupling section proximate the first end, and a substantially straight intermediate section between the first acoustic decoupling section and the attachment device. The first and second acoustic decoupling sections include first and second predetermined shapes.

The above summary is not intended to describe each disclosed embodiment or every implementation. The Figures and the Detailed Description, which follow, more particularly exemplify illustrative embodiments.

BRIEF DESCRIPTION OF DRAWINGS

The disclosure may be further explained with reference to the appended Figures, wherein like structure is referred to by like numerals throughout the several views, and wherein.

While the above-identified figures set forth various embodiments of the disclosed subject matter, other embodiments are also contemplated. In all cases, this disclosure presents the disclosed subject matter by way of representation and not limitation. It should be understood that numerous other modifications and embodiments can be devised by those skilled in the art which fall within the scope and spirit of the principles of this disclosure.

DETAILED DESCRIPTION

The present disclosure provides a hearing article having a tether that includes an acoustic decoupling section and a substantially straight section. The combination of an acoustic decoupling section proximate a hearing device and a substantially straight section reduces the amount of sound that may be transmitted through the tether and the hearing device and ultimately perceived by a user. Accordingly, such a tether results in a hearing article that more effectively prevents unwanted sound or noise from being perceived by a user.

Figure 1A:
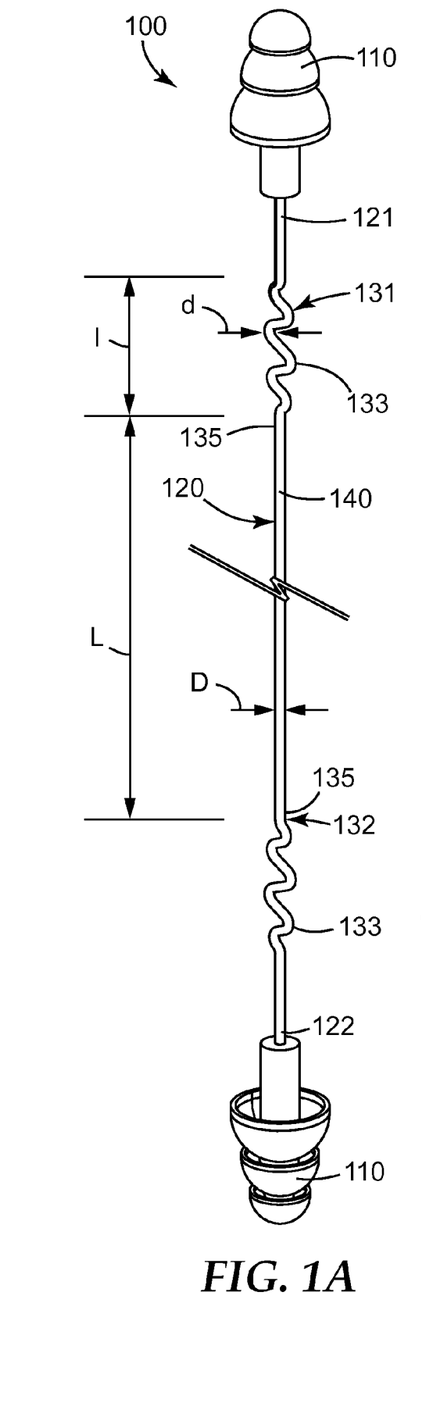
FIG. 1a is a partial perspective view of a hearing article having an acoustic decoupling section according to the present disclosure including a two-dimensional shape.

FIG. 1a shows an exemplary hearing device 100 according to the present disclosure. Hearing device 100 includes first and second hearing devices 110 joined by a tether 120. Tether 120 includes first and second ends 121, 122 attached to first and second hearing devices 110. Hearing devices 110 may be earplugs, electronic earplugs, earphones, communication devices, or other hearing devices. Tether 120 may be used to maintain first and second hearing devices 110 as a pair, and/or allows a user to hang hearing devices 110 around the user's neck, for example.

Tether 120 includes a combination of one or more acoustic decoupling sections and one or more substantially straight sections. In an exemplary embodiment, tether 120 includes first and second acoustic decoupling sections 131, 132, and a straight intermediate section 140 between first and second acoustic decoupling sections 131, 132. First and second acoustic decoupling sections 131, 132 are positioned proximate first and second ends 121, 122, respectively, of tether 120. In use, first and second acoustic decoupling sections 131, 132 may be positioned generally above, below or behind the ear and/or adjacent a side of the user's head. Straight section 140 may be positioned around the rear of a user's neck and portions of the side of a user's head, for example.

In an exemplary embodiment, acoustic decoupling sections 131, 132 may be described as having acoustic impedance values that differ from an acoustic impedance value of straight section 140. A mismatch of acoustic impedance values between acoustic decoupling sections 131, 132 and straight section 140 may result from the presence of one or more of differences in cross-sectional sizes, shapes, or areas, materials, or predetermined tether geometry, for example. Acoustic impedance values of acoustic decoupling sections 131, 132 and straight sections 140 may also differ in part due to the differing flexibility or spring characteristics between the different sections as a result of the shape of acoustic decoupling sections 131, 132. Sound transmitted through tether 120, for example from contact between tether 120 and clothing, or vibrations caused by wind, is thus affected by acoustic decoupling sections 131, 132 and an interface 135 between acoustic decoupling sections 131, 132. In this way, sound transmission efficiency of tether 120 is reduced as compared to a tether not including a combination of one or more acoustic decoupling sections and straight sections.

Unwanted sound perceived by a user resulting from contact with tether 120 may thus be limited.

Sound transmission through tether 120 generally results from contact or stimulation of tether 110. For example, rubbing or other contact between tether 120 and a shirt collar or other clothing may generate acoustic waves transmitted in tether 120. Contact or stimulation of tether 120 often occurs some distance away from hearing devices 131, 132, for example in an intermediate location of tether 120. Sound energy generated by contact or stimulation at straight intermediate section 140, for example, of tether 120 must encounter interface 135 and acoustic decoupling sections 131 and/or 132 before the sound energy is able to pass to hearing devices 110. Accordingly, a tether including acoustic decoupling sections 131, 132 in combination with straight section 140 results in less sound transmitted through hearing devices 110 as compared to a tether 120 having a substantially consistent shape, cross-section, and/or material construction, for example. Further, straight section 140 is less likely to catch on clothing or features in the environment, and thus may limit sound energy present in tether 120 due to such occurrences.

In an exemplary embodiment shown in FIG. 1, first and second acoustic decoupling sections 131, 132 include a predetermined shape, such as a two-dimensional wave 133. Wave 133 forms a predetermined shape in tether 120 such that the portion of tether 110 comprising acoustic decoupling sections 131 and 132 may remain flexible yet return to wave shape 133 when an external force acting on acoustic decoupling sections 131 or 132 is removed. Wave 133 is formed substantially in a single plane such that wave 133 may lay substantially flat on a surface, for example.

In an exemplary, embodiment straight section 140 is flexible and conformable but, in an exemplary embodiment, does not include a non-straight predetermined shape that straight section 140 repeatedly returns to in the absence of an external force. In an exemplary embodiment, straight section 140 may include a predetermined shape that is different than a shape of acoustic decoupling sections 131, 132.

In an exemplary embodiment, wave 133 affects an acoustic impedance value of acoustic decoupling sections 131, 132 such that acoustic decoupling sections 131, 132 have an acoustic impedance value that differs from a value of straight section 140. In addition to the predetermined shape of wave 133, wave 133 may impart additional resilience and/or differing flexibility, as compared to straight section 140, to affect sound transmission efficiency through tether 120. Sound transmission between straight section 140 and acoustic decoupling sections 131, 132 may thus be reduced.

Figure 1B:
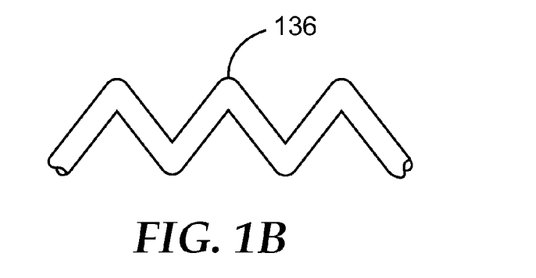
FIGS. 1b-1d are partial views of exemplary acoustic decoupling sections according to the present disclosure.
Figure 1C:
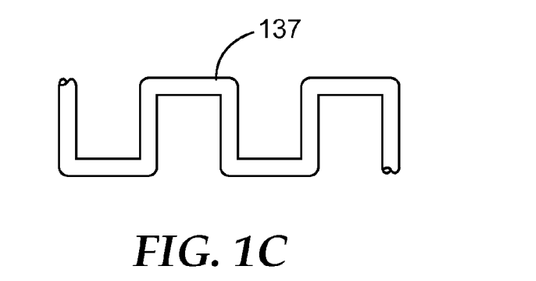
Figure 1D:
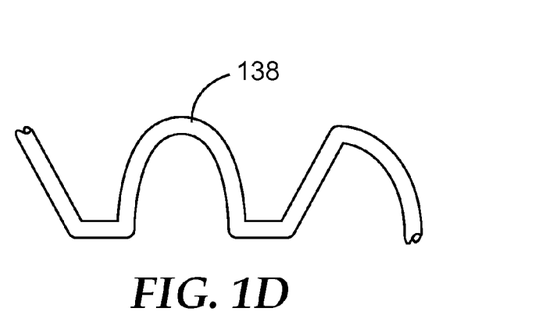

In an exemplary embodiment, acoustic decoupling sections 131, 132 may include any suitable shape affecting an acoustic impedance, for example, of tether 120 at acoustic decoupling sections 131, 132. Wave 133 may be similar in appearance to a sine wave or other suitable wave shape. Alternatively, or in addition, acoustic decoupling sections 131, 132 may include a zig-zag wave shape 136 (FIG. 1b), square wave shape 137 (FIG. 1c), irregular or multiple curved shape 138 (FIG. 1d), or other suitable predetermined shape that differs from straight section 140.

Acoustic decoupling sections 131, 132 may include one or more three-dimensional shapes, two-dimensional shapes, textures, varying cross-sections, or other features. In an exemplary embodiment, acoustic decoupling sections 131, 132 may include portions of differing diameters. For example, tether 110 may have a first diameter (d) in straight section 140 and a second diameter (D) in one or both acoustic decoupling sections 131 and/or 132 such that first diameter (d) is not equal to second diameter (D). In other exemplary embodiments, first diameter (d) is substantially identical to second diameter (D). In various exemplary embodiments, first diameter (d) and second diameter (D) may be between 0.25 mm and 7 mm, 0.7 mm and 2.5 mm, or about 1.3 mm. In some exemplary embodiments, tether 110 may include different surface textures or treatments in acoustic decoupling sections 131, 132 as compared to straight section 140. The presence of different diameters and or surface treatments may further reduce the transmission efficiency of tether 110 such that less unwanted noise due to stimulation of tether 110 is perceived by a user. In various exemplary embodiments, tether 110 has a solid cross-section such that tether 110 does not define a longitudinal channel or tube along a length of tether 110.

In an exemplary embodiment, acoustic decoupling sections 131, 132 have a length (l) in a neutral state such that the sections are not acted on by an external force that alters its shape from a predetermined shape, and straight section 140 has a length (L). Length (l) of acoustic decoupling sections 131, 132 is generally less than (L). In various exemplary embodiments, (l) is between about 0.5 cm and 10 cm, 1 cm and 5 cm, or about 2.5 cm and (L) is between about 35 cm and 80 cm, 45 cm and 65 cm, or about 55 cm. In some exemplary embodiments, length (L) of straight section 140 is between approximately 2 and 40, 4 and 30, or about 20 times a length (l) of each of first and second acoustic decoupling sections 131, 132.

Figure 2A:
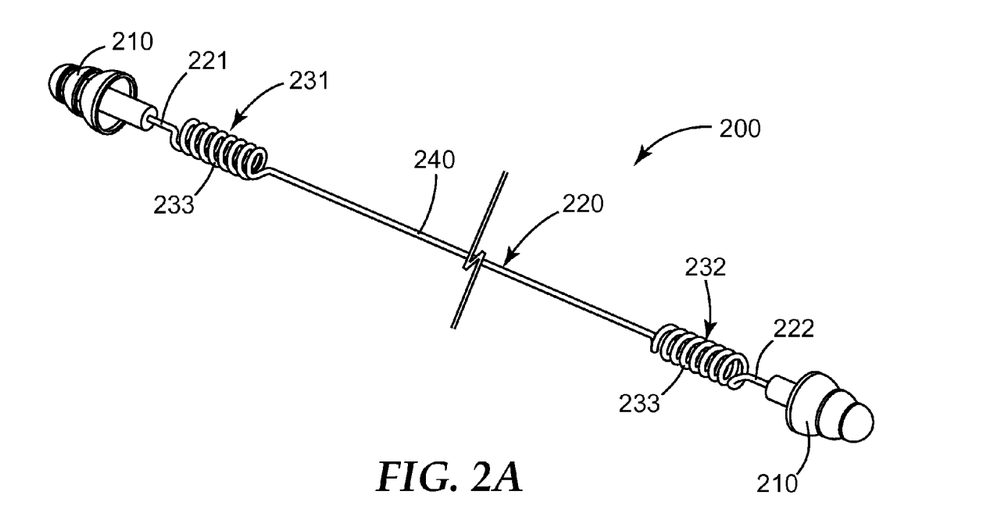
FIG. 2a is a perspective view of an exemplary hearing article having an acoustic decoupling section according to the present disclosure including a spiral.

FIG. 2a shows an exemplary hearing article 200 according to the present disclosure having acoustic decoupling sections 231, 232 including a three-dimensional shape. Similar to hearing device 100 described above, hearing article 200 includes first and second hearing devices 210 joined by a tether 220. Tether 220 includes first and second ends 221, 222 attached to first and second hearing devices 210, and includes a combination of one or more acoustic decoupling sections and one or more substantially straight sections. In an exemplary embodiment, tether 220 includes first and second acoustic decoupling sections 231 and 232 and a straight intermediate section 240 between first and second acoustic decoupling sections 231, 232.

In an exemplary embodiment, acoustic decoupling sections 231, 232 may be described as having acoustic impedance values that differ from an acoustic impedance value of straight section 240. In an exemplary embodiment shown in FIG. 2a, first and second acoustic decoupling sections 231, 232 include a predetermined shape, such as a three-dimensional spiral 233, for example. Spiral 233 forms a predetermined shape in tether 220 such that the portion of tether 220 comprising acoustic decoupling sections 231 and 232 may remain flexible yet will return to a spiral 233 when an external force acting on acoustic decoupling sections 231 or 232 is removed.

In an exemplary embodiment, spiral 233 affects an acoustic impedance value of acoustic decoupling sections 231, 232 such that it differs from an acoustic impedance value of straight section 240. In addition to the predetermined shape of spiral 233, spiral 233 may impart additional resilience and/or differing flexibility, as compared to straight section 240, to affect sound transmission efficiency through tether 120. Sound transmission between straight section 240 and acoustic decoupling sections 231, 232 may thus be reduced.

Figure 2B:
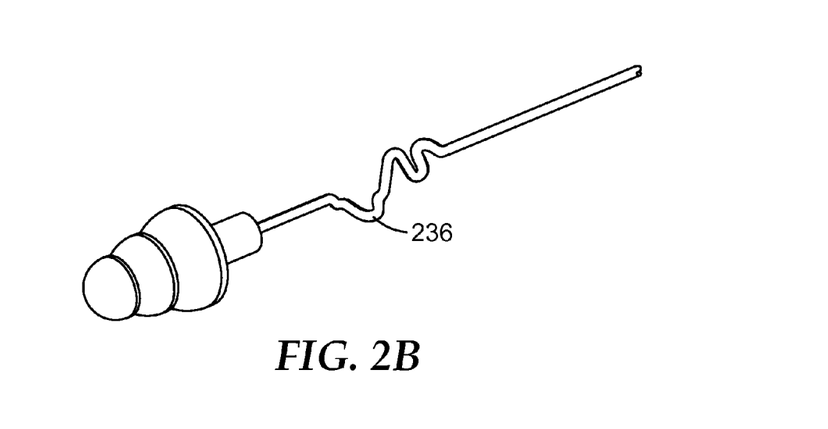
FIG. 2b is a partial perspective view of an exemplary acoustic decoupling section according to the present disclosure.

In an exemplary embodiment, acoustic decoupling sections 231, 232 may include any suitable shape affecting an acoustic impedance, for example, of tether 220 at acoustic decoupling sections 231, 232. Acoustic decoupling sections 231, 232 may include one or more two-dimensional shapes, textures, varying cross-sections, or other features. As an alternative, or in addition, to spiral 233, acoustic decoupling sections may include a three-dimensional wave shape 236 (FIG. 2b), for example, or other suitable shape that differs from straight section 140.

Figure 3:
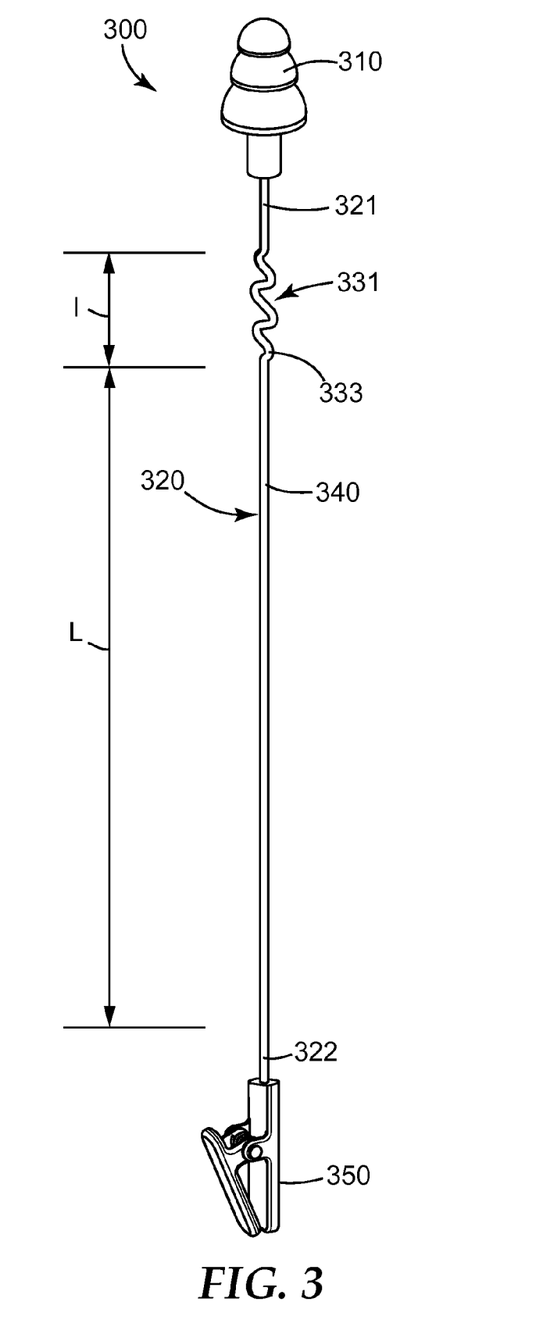
FIG. 3 is a perspective view of an exemplary hearing article having an acoustic decoupling section according to the present disclosure.

FIG. 3a shows an exemplary hearing article 300 according to the present disclosure having acoustic decoupling section 331. Similar to hearing article 100 described above, hearing article 300 includes a first hearing devices 310 joined to a tether 320. Tether 320 includes first and second ends 321, 322 attached to a first hearing device 310 and an attachment device 350. Tether 320 includes a combination of one or more acoustic decoupling sections and one or more substantially straight sections. In an exemplary embodiment, tether 320 includes first acoustic decoupling section 331 and a straight intermediate section 340 between first acoustic decoupling section 331 and clip 350.

Attachment device 350 may be a clip, latch, loop, or other suitable attachment device that may be attached to an article of clothing, for example, to secure hearing article 300 to a user. In various exemplary embodiments, a user may have a pair of hearing articles 300 that may be used for each ear.

In an exemplary embodiment shown in FIG. 3, first acoustic decoupling section 331 include a predetermined shape, such as a two-dimensional wave 333, for example. As described herein, wave 333 affects an acoustic impedance value of acoustic decoupling section 331 such that it differs from an acoustic impedance value of straight section 340. Sound transmission efficiency through tether 320 may thus be reduced such that unwanted sound is limited from being transmitted through tether 320 and ultimately perceived by a user. Acoustic decoupling section 331 may include any suitable shape affecting an acoustic impedance of tether 320 at acoustic decoupling section 331 and may include one or more two-dimensional shapes, three-dimensional shapes, textures, varying cross-sections, or other features. As an alternative, or in addition, to wave 333, acoustic decoupling section 331 may include a zig-zag shape, square wave shape, spiral shape, irregular shape, or other suitable shape that differs from straight section 140.

In an exemplary embodiment, acoustic decoupling section 331 has a length (l) in a neutral state such that the section is not acted on by an external force that alters its shape from a predetermined shape, and straight section 140 has a length (L). Length (l) of acoustic decoupling section 231 is generally less than (L). In various exemplary embodiments, (l) is between about 0.5 cm and 10 cm, 1 cm and 5 cm, or about 2.5 cm and (L) is between about 5 cm and 80 cm, 10 cm and 70 cm, or about 40 cm. In some exemplary embodiments, length (L) of straight section 140 is between approximately 2 and 40, 5 and 25, or about 15 times a length (l) of each of first and second acoustic decoupling sections 131, 132.

An exemplary tether 120, 220, 320 may be formed from any suitable flexible material. For example, a tether may be formed from a polyvinylchloride, such as a material having the trade name G-2184 available from S&E Specialty Polymers of Lunenburg, Ma. Other suitable materials include EPDM rubber, silicone, polyurethane and ethylene-vinyl acetate combinations. In some exemplary embodiments, suitable combinations of materials may be used to form tether 120, 220, 320 as described herein. For example, tether 120, 220, 320 may include a first inner material coated or covered by a second outer material. The second outer material may be present along an entire length of tether 120, 220, 320 or only a portion of tether 120, 220, 320, such as in an acoustic decoupling section or substantially straight section. In an exemplary embodiment, tether 120, 220, 320 is non-metallic. For example, tether 120, 220, 320 does not include a metallic wire core.

In an exemplary embodiment, exemplary tether 120, 220, 320 is formed by drawing or extruding the material to a desired cross-section and cutting the material to a desired length. After tether 120, 220, 320 is cut, a shape may be integrally formed to result in an acoustic decoupling section. For example, tether 120, 220, 320 may be heated slightly and wound, molded, stamped, crimped, or otherwise formed as known in the art to impart a predetermined shape.

An acoustic decoupling section formed in a later processing step may facilitate manufacturing and handling by allowing manufacture of tether 120, 220, 320 of extended length followed by cutting to a desired length and/or attaching to hearing devices before forming the acoustic decoupling sections. For example, a two-dimensional wave may be formed by molding, stamping, crimping, or other suitable process, after formation of a tether.

In other exemplary embodiments, tether 120, 220, 320 may be molded, such as by injection or compression molding. A shape of an acoustic decoupling section may be integrally formed while tether 120, 220, 320 is initially molded, or in one or more subsequent processing steps.

In some exemplary embodiments, acoustic decoupling sections may be non-integrally attached to tether 120, 220, 320. For example, tether 120, 220, 320 may be formed in an initial processing step and a separate component may be attached or joined to the tether to form one or more acoustic decoupling sections.

A hearing article as described herein provides several features and benefits. A tether having one or more acoustic decoupling sections limits unwanted transmission of sound energy through the tether that could be perceived by a user. Sound transmission can be efficiently limited while minimizing complicated manufacturing steps or excessive components. An acoustic decoupling section as described herein may be integrally formed in a tether to reduce sound transmission.

EXAMPLES

The characteristics, operation, and advantages of the present invention will be further described with regard to the following detailed non-limiting examples. These examples are offered to further illustrate the various specific and preferred embodiments and techniques. It should be understood, however that many variations and modifications may be made while remaining within the scope of the present invention.

Procedure 1: Sound Transmission Test

The sound transmission of a hearing article tether may be characterized by simulating a sound input that may occur when a tether contacts a user's collar. A 0.64 in. diameter drum, with a 400 grit aluminum oxide cloth as the outer surface, was rotated at approximately 200 rpm using a 6546 2-speed screw driver available from Milwaukee Electric Tool Corp. The cloth rubbed a 740 mm material length tether for 10 seconds in a direction opposite a first end of the tether at an intermediate section level with and approximately 305 mm material length from a first end of the tether. The first end of the tether was attached to EAR PUSH-INS with grip rings earplugs, available from 3M Co. of St. Paul, Mn., inserted in a 45CA hearing protector test fixture, available from G.R.A.S. Sound and Vibration of Holte, Denmark. The output was captured using LABVIEW software available from National Instruments Corporation of Austin, Tex. to measure sound transmission in dB. The measured output over the 10 second period was averaged. The second end of the tether hung freely.

Examples 1 Through 3

The tether of Example 1 was made of a 1.3 mm diameter 80 Shore A durometer PVC material and included a first acoustic decoupling section having a spiral shape. First and second spiral shapes were formed proximate first and second ends by tightly winding the material around a 1.2 mm diameter wire and heating using a WELLER 6866C electric industrial heat gun. The acoustic decoupling section had a length (l) in a neutral state of 32 mm and a total material length of 165 mm.

The tether of Example 2 was made of a 1.3 mm diameter 80 Shore A durometer PVC materials and included a first acoustic decoupling section having a wave shape shown in FIG. 1a. The wave shape was formed by crimping the tether between two blocks with machined wave shaped cavities. The blocks were heated to 100° C. in an oven. The tether was placed between the blocks and the blocks squeezed together with an arbor press such that compression of the tether was limited to approximately 80% of the original diameter. The tether included only one acoustic decoupling section proximate a first end. The acoustic decoupling section had a length (l) in a neutral state of 19 mm and a total material length of 30 mm.

The tether of Comparative Example A was made of a 1.3 mm diameter 80 Shore A durometer PVC material. The tether did not include a formed shape.

The tether of Comparative Example B was made of a 1.3 mm diameter 80 Shore A durometer PVC material. A spiral shape was formed over substantially the entire length of the tether by tightly winding the material around a 1.2 mm diameter wire and heating using a WELLER 6866C electric industrial heat gun.

Figure 4:
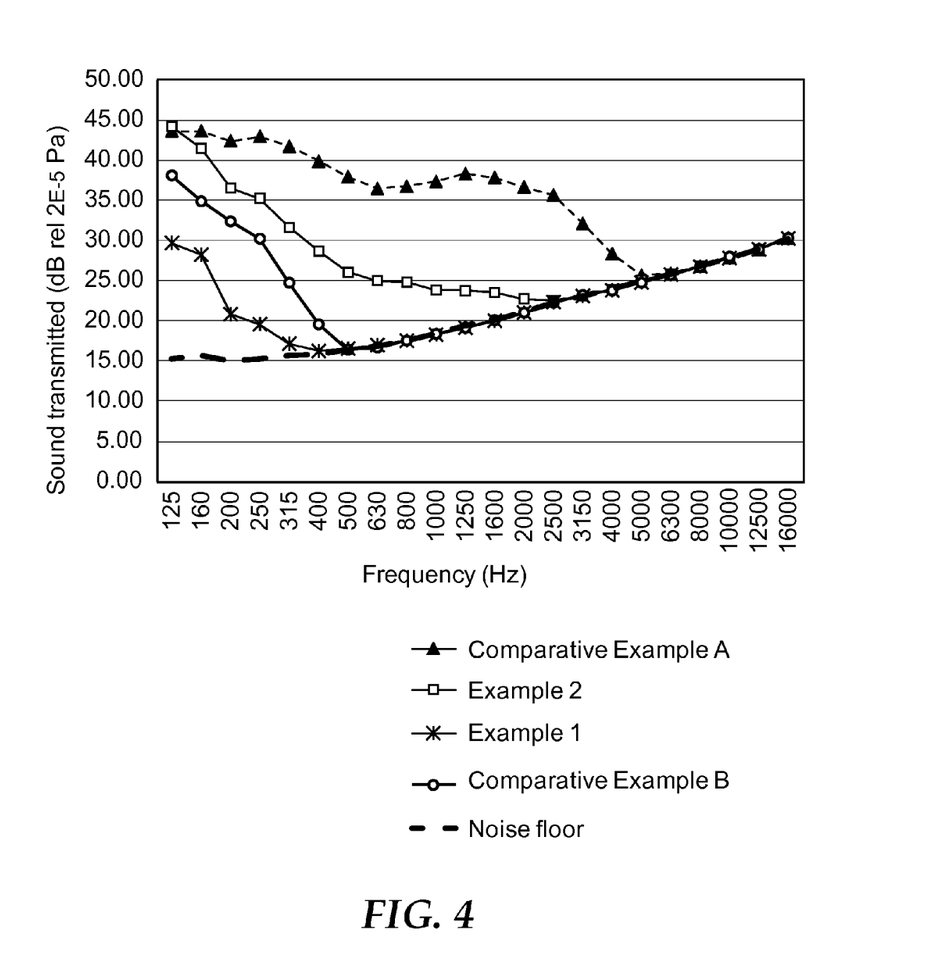
FIG. 4 is a graph illustrating noise transmission of tethers of Examples 1 and 2.

The results of the sound transmission test are summarized in FIG. 5. Measured sound transmission of Examples 1 and 2, including an acoustic decoupling section, over frequencies between approximately 125 and 5000 Hz was significantly reduced, as compared to the tether of Comparative Example A, which was substantially straight and did not include an acoustic decoupling section.

Comparison between Example 1 and Comparative example B, each including spiral shapes, indicated significant improvement of Example 1 in limiting sound transmission. The tether of Example 1, including a substantially straight section and an acoustic decoupling section having a spiral shape with a length (l) of 32 mm, performed significantly better than Comparative Example B, including a spiral along an entire length. Less noise was measured through the tether of Example 1 having a combination of both a relatively short acoustic decoupling section and a substantially straight section as compared to a tether having the same spiral shape along substantially an entire length.

What is claimed is:
1. A hearing-protective article, comprising:
first and second earplugs; and
a tether having a first end attached to the first earplug and a second end attached to the second earplug;
wherein the tether includes a first acoustic decoupling section proximate the first end, a second acoustic decoupling section proximate the second end, and a substantially straight intermediate section between the first and second acoustic decoupling sections, the first and second acoustic decoupling sections comprising first and second predetermined shapes, and
wherein the first acoustic decoupling section, the second acoustic decoupling section, and the substantially straight intermediate section between the first and second acoustic decoupling sections, are all sections of a tether that is in the form of a single cord with the first and second acoustic decoupling sections and the substantially straight intermediate section integrally formed therein, and wherein the single cord is a non-metallic cord that comprises a solid cross-section and that does not include a metallic core.

2. The hearing-protective article of claim 1, wherein the first and second predetermined shapes are two-dimensional shapes.

3. The hearing-protective article of claim 1, wherein the first and second predetermined shapes comprise a wave shape.

4. The hearing-protective article of claim 1, wherein the first and second predetermined shapes comprise a zig-zag shape.

5. The hearing-protective article of claim 1, wherein the first and second predetermined shapes comprise a square wave shape.

6. The hearing-protective article of claim 1, wherein the first and second predetermined shapes comprise multiple curved segments.

7. The hearing-protective article of claim 1, wherein the first and second predetermined shapes comprise three-dimensional shapes.

8. The hearing-protective article of claim 1, wherein the first and second predetermined shapes comprise a spiral shape.

9. The hearing-protective article of claim 1, wherein the first and second acoustic decoupling sections include a cross-section that differs from a cross-section of the straight intermediate section.

10. The hearing-protective article of claim 1, wherein the first acoustic decoupling section has a length (l) and the straight section has a length (L) in a neutral configuration, and (L)>10(l).

11. The hearing-protective article of claim 1, wherein the first acoustic decoupling section has a length (l) between 0.5 and 10 cm and the straight section has a length (L) between 35 cm and 80 cm.

12. The hearing-protective article of claim 1, wherein the tether has a first diameter (d) between 0.7 mm and 2.5 mm.

13. The hearing-protective article of claim 1, wherein the tether is made of ethylene-propylene-diene (EPDM) rubber.

14. The hearing-protective article of claim 1, wherein the tether is made of polyvinylchloride (PVC).

15. The hearing-protective article of claim 1, wherein the tether is made of silicone rubber.

16. The hearing-protective article of claim 1, wherein the tether has a solid cross-section.

17. The hearing-protective article of claim 1, wherein the first and second hearing devices are electronic earplugs.

18. The hearing-protective article of claim 1, wherein the tether is permanently attached to the first and second earplugs.

19. A hearing-protective article, comprising:
a first earplug;
an attachment device and
a tether having a first end attached to the first earplug and a second end attached to the attachment device;
wherein the tether includes a first acoustic decoupling section proximate the first end, and a substantially straight intermediate section between the first acoustic decoupling section and the attachment device, the first acoustic decoupling section comprising a first predetermined shape, and wherein the first acoustic decoupling section and the substantially straight intermediate section between the first acoustic decoupling section and the attachment device, are both sections of a tether that is in the form of a single cord with the first acoustic decoupling section and the substantially straight intermediate section integrally formed therein, and wherein the single cord is a non-metallic cord that comprises a solid cross-section and that does not include a metallic core.

20. The hearing-protective article of claim 19, wherein the first acoustic decoupling section has a length (l) and the straight section has a length (L) in a neutral configuration, and (L) >5(l).

21. The hearing-protective article of claim 19, wherein the first acoustic decoupling section has a length (l) between 1 cm and 8 cm and the straight section has a length (L) between 5 cm and 25 cm.

* * * * *